United States Patent
Paunescu et al.

(10) Patent No.: US 10,449,348 B2
(45) Date of Patent: Oct. 22, 2019

(54) DEVICES AND METHODS FOR ENHANCING THE TOPICAL APPLICATION OF A BENEFIT AGENT

(71) Applicant: Johnson & Johnson Consumer Inc., Skillman, NJ (US)

(72) Inventors: Alexandru Paunescu, Clinton, NJ (US); Jyotsna Paturi, Skillman, NJ (US); Ying Sun, Belle Mead, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 211 days.

(21) Appl. No.: 15/271,294

(22) Filed: Sep. 21, 2016

(65) Prior Publication Data

US 2017/0080197 A1   Mar. 23, 2017

Related U.S. Application Data (60) Provisional application No. 62/221,889, filed on Sep. 22, 2015.

(51) Int. Cl.
*A61M 37/00* (2006.01)
*A61N 7/00* (2006.01)
*A61N 5/06* (2006.01)

(52) U.S. Cl.
CPC ....... *A61M 37/0092* (2013.01); *A61N 5/0617* (2013.01); *A61N 5/0624* (2013.01); *A61N 7/00* (2013.01); *A61M 2037/0007* (2013.01); *A61N 2005/0654* (2013.01); *A61N 2005/0662* (2013.01); *A61N 2007/0034* (2013.01)

(58) Field of Classification Search
CPC ............. A61N 7/00; A61N 2007/0034; A61N 5/0617; A61N 5/0624; A61M 37/0092; A61M 35/003; A61M 2037/0007
See application file for complete search history.

(56) References Cited

U.S. PATENT DOCUMENTS

| | | | |
|---|---|---|---|
| 5,084,577 A | 1/1992 | Bolich, Jr. | |
| 5,133,967 A | 7/1992 | Smith | |
| 5,458,140 A * | 10/1995 | Eppstein | A61B 5/14514 600/573 |
| 6,419,913 B1 * | 7/2002 | Niemiec | A61K 8/19 424/70.31 |
| 2002/0006418 A1 | 1/2002 | Kung et al. | |
| 2009/0318852 A1 | 12/2009 | Reed et al. | |

(Continued)

FOREIGN PATENT DOCUMENTS

| CN | 2393485 Y | 8/2000 |
|---|---|---|
| CN | 101400405 A | 4/2009 |
| CN | 101622031 A | 1/2010 |

(Continued)

OTHER PUBLICATIONS

Tezel, Ahmet, et al.; "Synergistic Effect of Low-Frequency Ultrasound and Surfactants on Skin Permeability," Journal of Pharmaceutical Sciences, vol. 91, No. 1, pp. 91-100; Jan. 2002.

*Primary Examiner* — Theodore J Stigell (57) ABSTRACT

The present invention relates to devices and methods for treating, reducing and preventing adverse skin/scalp conditions and enhancing the topical application of a benefit agent. The devices are ultrasonic with transducers positioned at an angle other than 90° relative to the surface at which the ultrasound is to be applied.

6 Claims, 2 Drawing Sheets

(56) References Cited

U.S. PATENT DOCUMENTS

2011/0046521 A1    2/2011   Farrelly
2014/0066837 A1    3/2014   Moy

FOREIGN PATENT DOCUMENTS

| CN | 104147694 A | | 11/2014 |
|---|---|---|---|
| DE | 202009003586 U1 | | 6/2009 |
| WO | WO 98/22031 A1 | | 5/1998 |
| WO | WO 99/39763 A1 | | 8/1999 |
| WO | WO 00/15300 | * | 3/2000 |
| WO | WO 00/15300 A1 | | 3/2000 |
| WO | WO 03/013654 A1 | | 2/2003 |
| WO | WO 03/077833 A2 | | 9/2003 |
| WO | WO 2005/004972 A1 | | 1/2005 |
| WO | WO 2006/105109 A2 | | 10/2006 |
| WO | WO 2007/118224 A2 | | 10/2007 |
| WO | WO 2011/042894 A1 | | 4/2011 |
| WO | WO 2012/081011 | * | 6/2012 |
| WO | WO 2012/081011 A1 | | 6/2012 |
| WO | WO 2014/127091 A1 | | 8/2014 |

* cited by examiner

DEVICES AND METHODS FOR ENHANCING THE TOPICAL APPLICATION OF A BENEFIT AGENT

CROSS-RELATED APPLICATION

The present application claims the benefit of the earlier filing date of U.S. provisional patent application 62/221,889, filed Sep. 22, 2015, the entirety of which application is hereby incorporated by reference herein as if fully set forth herein.

The present invention relates to devices and methods for treating, reducing and preventing adverse skin/scalp conditions and enhancing the topical application of a benefit agent. The devices are ultrasonic with transducers positioned at an angle other than 90° relative to the surface at which the ultrasound is to be applied.

BACKGROUND OF THE INVENTION

Compositions for delivering benefit agents are well known. Typical formulations include solutions, emulsions, suspensions and gels. The viscosity may vary based on intended area for application, intended use (leave on or rinse off), or consumer preference. When applied to skin, the benefit agent penetrates the skin to some extent, depending on the agent and the formulation.

There is a need for devices and methods that control skin penetration of benefit agents. U.S. Pat. No. 6,419,913 relates to micellar compositions that enhance skin penetration. However, these compositions can be difficult to manufacture and the cost of the products are relatively high. There is also no means for controlling the degree of skin penetration. Ultrasound devices have been utilized to help analgesic compositions and anti-inflammatory agents penetrate skin to help reduce muscle pain and the like. United States patent application 2009/0318852 teaches an ultrasound device for applying agents to skin, which application is herein incorporated by reference. The transducers of the described devices are not oriented within the housing of such devices so as project the generated ultrasound waves at an angle other than at 90° (perpendicular) relative to the surface where the ultrasound is to be applied (e.g., the surface of the skin of a user).

SUMMARY OF THE INVENTION

Figures 2, 3:
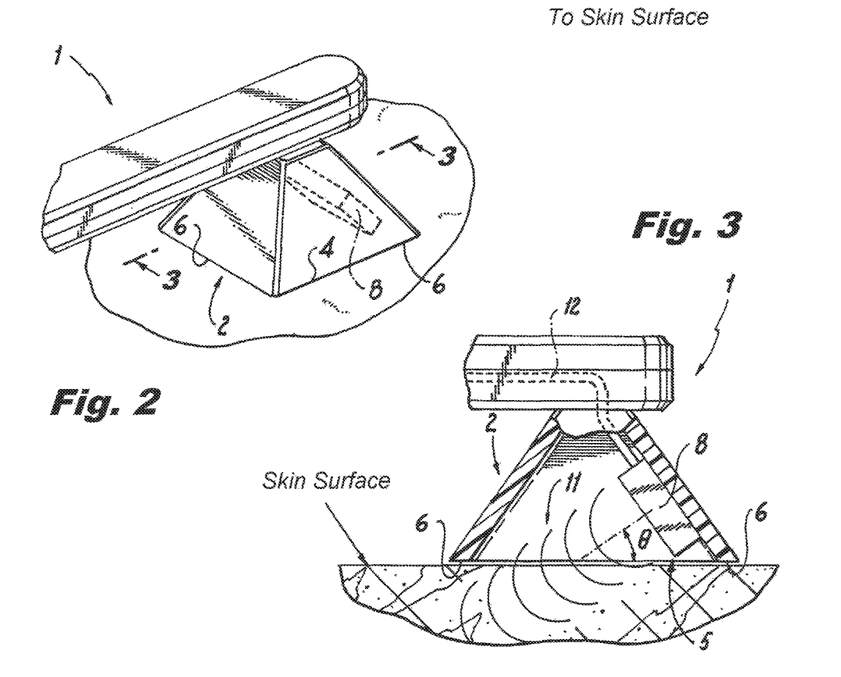
FIG. 2 is a top perspective view of a portion of the handle and housing of the device of FIG. 1.
FIG. 3 is a cross-sectional view of the device of FIG. 1 taken along cross-section indicators 3-3.

Applicants have now discovered that specific skin benefits and improved penetration of benefit agents through skin may achieved by controlling the angle at which the ultrasound is applied. The methods and devices according to the present invention include an ultrasound transducer oriented at an angle to the surface where it will be applied such that the angle $\ominus$ (as illustrated in FIG. 3) ranges from 5° to 75°, for example 15°, 45° or 60°. The desired angle will change based on the ultrasound intensity desired for a specific skin benefit or degree of skin penetration desired for skin benefit agents.

The devices and methods for delivering ultrasound energy can be used, either alone or with active benefit agents, for hair growth or regrowth, cosmetic, skin care, wound care, dermatologic, and other personal care applications, as well as in other applications and industries.

SUMMARY OF INVENTION

In one embodiment, the present invention relates to methods for enhancing penetration of active benefit agents comprising the steps of:
a. providing a topical composition comprising an active benefit agent;
b. applying the topical composition to an area of the skin or scalp in need of treatment from the active benefit agent;
c. providing a device having power source and an acoustic transducer electrically connected to the power source, the transducer calibrated to generate acoustic energy at a frequency ranging from about 20 kHz to about 3000 kHz;
d. orienting the device such that any ultrasound waves generated by the transducer are projected at an angle $\ominus$ other than perpendicular relative to the surface of skin at the area on which the topical composition was applied; and
e. delivering the ultrasound to the area on which the topical composition was applied while maintaining the projection angle $\ominus$ at other than perpendicular relative to the surface of the skin at the area on which the topical composition was applied.

In another embodiment, the present invention relates to methods for condition and/or preparing skin for application of active benefit agent comprising the steps of:
a. providing a topical composition for propagation of ultrasound waves to and from an ultrasound device;
b. applying the topical composition to an area of the skin or scalp in need of treatment;
c. providing a device having power source and an acoustic transducer electrically connected to the power source, the transducer calibrated to generate acoustic energy at a frequency ranging from about 20 kHz to about 3000 kHz;
d. orienting the device such that any ultrasound waves generated by the transducer are projected at an angle $\ominus$ other than perpendicular relative to the surface of skin at the area on which the topical composition was applied; and
e. delivering the ultrasound to the area on which the topical composition was applied while maintaining the projection angle $\ominus$ at other than perpendicular relative to the surface of the skin at the area on which the topical composition was applied.

In certain embodiments, the present invention relates to methods for accelerating healing of connective tissue comprising the steps of:

a. providing a topical composition for propagation of ultrasound waves to and from an ultrasound device;
b. applying the topical composition to an area of the skin or scalp in need of treatment;
c. providing a device having power source and an acoustic transducer electrically connected to the power source, the transducer calibrated to generate acoustic energy at a frequency ranging from about 20 kHz to about 3000 kHz;
d. orienting the device such that any ultrasound waves generated by the transducer are projected at an angle ⊖ other than perpendicular relative to the surface of skin at the area on which the topical composition was applied; and
e. delivering the ultrasound to the area on which the topical composition was applied while maintaining the projection angle ⊖ at other than perpendicular relative to the surface of the skin at the area on which the topical composition was applied.

In certain embodiments, the present invention relates to methods for breaking down melanin granules comprising the steps of:
a. providing a topical composition for propagation of ultrasound waves to and from an ultrasound device;
b. applying the topical composition to an area of the skin or scalp in need of treatment;
c. providing a device having power source and an acoustic transducer electrically connected to the power source, the transducer calibrated to generate acoustic energy at a frequency ranging from about 20 kHz to about 3000 kHz;
d. orienting the device such that any ultrasound waves generated by the transducer are projected at an angle ⊖ other than perpendicular relative to the surface of skin at the area on which the topical composition was applied; and
e. delivering the ultrasound to the area on which the topical composition was applied while maintaining the projection angle ⊖ at other than perpendicular relative to the surface of the skin at the area on which the topical composition was applied.

In certain embodiments, the present invention relates to methods for treating, preventing or reducing skin and/or scalp conditions selected from retarded hair growth, hypotrichosis, hair loss, skin wound healing, skin scarring, skin wrinkling, comprising the steps of:
a. providing a topical composition for propagation of ultrasound waves to and from an ultrasound device;
b. applying the topical composition to an area of the skin or scalp in need of treatment;
c. providing a device having power source and an acoustic transducer electrically connected to the power source, the transducer calibrated to generate acoustic energy at a frequency ranging from about 20 kHz to about 3000 kHz;
d. orienting the device such that any ultrasound waves generated by the transducer are projected at an angle ⊖ other than perpendicular relative to the surface of skin at the area on which the topical composition was applied; and
e. delivering the ultrasound to the area on which the topical composition was applied while maintaining the projection angle ⊖ at other than perpendicular relative to the surface of the skin at the area on which the topical composition was applied.

DETAILED DESCRIPTION OF THE INVENTION

The articles of the present invention can comprise, consist of, or consist essentially of the essential elements and limitations of the invention described herein, as well any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of." The terms "a" and "the" as used herein are understood to encompass the plural as well as the singular.

All documents incorporated herein by reference are only incorporated herein to the extent that they are not inconsistent with this specification.

As used herein, "active benefit agent" is a compound (e.g., a synthetic compound or a compound isolated from a natural source) that has a cosmetic or therapeutic effect on tissue (e.g., a material capable of exerting a biological effect on the human or mammalian body) such as therapeutic drugs or cosmetic agents. Examples of benefit agents include small molecules, peptides, proteins, nucleic acid materials, and nutrients such as minerals and extracts. The amount of the benefit agent used will depend on the benefit agent and/or the intended use of the end product. Benefit agents may be liquid, solid, or semi-solid.

As used herein, "pharmaceutically acceptable," "cosmetically acceptable," or "dermatologically acceptable" means suitable for use in contact with tissues (e.g., the skin (including scalp), hair, mucosa, epithelium or the like) without undue toxicity, incompatibility, instability, irritation, or allergic response.

As used herein, "safe and effective amount" means an amount sufficient to provide a desired benefit at a desired level, but low enough to avoid serious side effects. The safe and effective amount of the ingredient or composition will vary with the area being treated, the age of the end user, the duration and nature of the treatment, the specific ingredient or composition employed, the particular carrier utilized, and like factors.

As used herein, "targeted delivery" means that the depth of skin penetration of a benefit agent is controlled for improved efficacy and safety.

As used herein, the term "treating" or "treatment" means the alleviation or elimination of symptoms, cure, prevention, or inhibition of a disease or medical condition, or improvement of tissue growth/healing or cosmetic conditions such as reducing appearance of skin wrinkles/fine lines, under-eye bags, cellulites, skin marks/hyperpigmentation or uneven tone, promotion of hair growth or regrowth, or reduction of pain or inflammation.

As used herein, the term "visual inspection" means that a human viewer can visually discern the presence of hair or hair growth with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

In certain embodiments, the present invention as disclosed herein may be practiced in the absence of any component, element (or group of components or elements) or method step which is not specifically disclosed herein.

Figure 1:
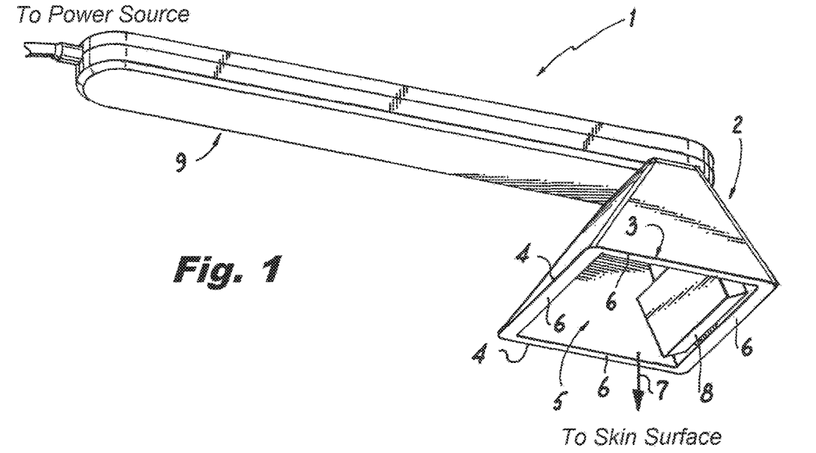
FIG. 1 is a bottom perspective view of a device according to the present invention.

In certain embodiments, the Device 1 includes a housing 2 having bottom portion 3, the bottom portion 3 having a periphery 4 defining a housing opening 5, the edges of periphery 4 forming a planar (or substantially planar) application surface 6. Optionally, a handle 9 is attached to housing 2. The outer side of planar application surface 6 faces in the direction 7 (i.e., towards an application surface such as a user's skin). In some embodiments, the application surface 6 is adapted to lie on and be parallel with (or substantially parallel with) with the planar surface formed by the skin surface of a user. In certain embodiments, the device comprises a transducer 8 and a power source (not shown) for providing electrical power to the transducer 8 through an electrical drive circuit (not shown). The power source should be chosen so as to create cavitation bubbles (as described below) in an ultrasound propagating media. In certain embodiments, the power source capable of providing electronic signal power of from about 0.1 W to about 100 W, preferably from about 1 W to about 20 W. In certain embodiments, the various components of the device 1 are connected using cable/wiring 12. In one embodiment, the transducer 8, power source and an electrical drive circuit are disposed within the housing 2. In other embodiments, the transducer 8 is disposed within housing 2 and the power source and optional electrical drive circuit are disposed within the handle 9. In the case of a cordless device, the power source is a battery (such as a rechargeable lithium ion battery or a non-rechargeable battery) or, in the case of corded devices, the power source is an AC current provided from a source voltage (e.g., electrical wall outlet) through an electrical power line cord. In certain embodiments, a rectifier or other means may be employed to convert AC current to DC.

In certain embodiments, the power may further flow through an optional timing controller (not shown) prior to the electrical drive circuit. The power may also flow to an optional vibrating motor (not shown). When used, the timing controller provides timing, motor control, and various control functions for the device 1 and is connected to an electrical drive circuit, which optionally includes an acoustic module drive circuit to provide the necessary electrical drive to the transducer 8. When present, the electrical drive circuit may be further connected to a motor drive, which provides electrical power to the motor. The motor is not strictly required, and is provided to vibrate the therapy head (i.e., the transducer 8) to provide a pleasant massaging effect. Further, vibrating the head can help disperse the product on the skin. The electrical drive circuit is further connected to electrical contacts, which connect to a removable transducer compartment, providing electrical contact between the transducer and the electrical drive circuit. The housing 2 (or optional compartments for the above components) may be molded from conventional plastics known in the art. Suitable plastics include polyethylene, nylon, polypropylene and the like.

Transducers 8 useful herein are well known in the art. Suitable transducers for use in devices according to the present invention generate acoustic energy. The acoustic energy employed has a frequency ranging from 20 kHz or (about 20 kHz) to 3000 kHz (or about 3000 kHz), optionally from 100 kHz (or about 100 kHz) to 1000 kHz (or about 1000 kHz), or optionally from 250 kHz (or about 250 kHz) to 750 kHz (or about 750 kHz). The transducer is positioned in the housing 2 in electrical communication with the power source and the optional electrical drive circuit, for generating or producing ultrasound waves 11 and transducer 8 is oriented such that the ultrasound waves 11 are projected from the transducer 8 and through the opening 5 at an angle $\Theta$ (as shown in FIG. 3) other than at 90° (or other than perpendicular), or less than 90°, relative to the application surface 6. Suitable angles $\Theta$, at which the ultrasound waves 11 are projected/directed, range from 5° to 75°, optionally from 10° to 75°, optionally 10° to 60°, optionally 10° to 45°, optionally, 15° to 30° relative to the application surface. In certain embodiments, the angle $\Theta$ at which the ultrasound waves 11 are projected/directed is selected from the group consisting of 15°, 45°, 60° and 75°.

In certain embodiments, the transducer 8 is oriented such that the ultrasound waves 11 are projected from the transducer 8 and through the opening 5 at an angle $\Theta$ (as shown in FIG. 3) other than at 90° (or other than perpendicular), or less than 90°, relative to the application surface 6 and is maintained in such orientation for such projection of ultrasound waves 11 for from at least 50% (or about 50%), optionally 60% (or about 60%), optionally 70% (or about 70%), optionally 80% (or about 80%), optionally 90% (or about 90%), or optionally 95% (or about 95%) to, in each case, 100% (or about 100%) of the time period during which the ultrasound is applied. In certain embodiments, the transducer 8 is oriented such that the ultrasound waves 11 are projected from the transducer 8 and through the opening 5 at an angle $\Theta$ (as shown in FIG. 3) other than at 90° (or other than perpendicular), or less than 90°, relative to the application surface 6 and is maintained in such orientation for such projection of ultrasound waves 11 for during the entire time the ultrasound is applied.

In certain embodiments, traditional ultrasound devices such as described in previously incorporated by reference United States Patent application 2009/0318852 may be used in practicing the methods of use of the present invention so long as the transducer is orientated relative to a surface (such as, for example, the surface or mammalian skin and/or scalp) such that the generated ultrasound waves 11 are projected at an angle $\Theta$ other than at 90° relative to that surface.

Ultrasound is useful for providing a variety of skin benefits, including acne treatment, scar reduction, dermabrasion and pre-conditioning or preparing the skin for the delivery of topical actives into skin in the appropriate frequency range. This is due to ultrasounds' creating cavitation bubbles in the topical composition in which the ultrasound waves propagate. Once the above described cavitation bubbles are formed, they migrate towards the surface of the skin and, due to their unstable nature, implode, generating "micro-jets" that act as fluid micro-needles which enhance the penetration of the active benefit agents through the skin surface The depth of penetration of these micro jets increases as the frequency of the ultrasound decreases due to the fact that, at lower frequencies, the size of the cavitation bubbles increases, packing larger quantities of energy that is conveyed to the tissue at the moment of the implosion. This cavitation effect may lead to breaks in the skin surface uniformity through the creation of micro-lesions. The term "micro-lesions", as used herein, means discrete lesions caused by implosion of the cavitation bubbles, and not a wide surface lesion. The present inventors have found that, because the volume and surface density of the cavitation bubbles depends on the frequency and power density alone, the position of the ultrasonic transducer viz-a-viz the skin has a limited influence on sonophoresis efficiency and outcome. Accordingly, the transducer can be positioned to avoid directing the generated ultrasonic energy perpendicular to the skin (and, hence, reduce any negative effects associated with such perpendicularly directed energy).

Ultrasound has also been utilized therapeutically to accelerate connective tissue healing for a very long time, and its direct effects on extracellular matrix and cell proliferation have also been evaluated. Pre-clinical studies have indicated that ultrasound can stimulate collagen and elastin synthesis in tendon fibroblasts in response to in-vitro conditions that mimic an injury of the connective tissue matrix. Additionally, ultrasound has been shown to stimulate cell division during periods of rapid cell proliferation and confirmed by other studies which have found increased cell proliferation in fibroblasts with ultrasound.

Pulsed-Low Intensity Ultra Sound (PLIUS) has been shown to induce collagen, and elastin production in fibroblasts, and also increase levels of Glycosaminoglycans. Furthermore, low-intensity ultrasound can aid the repair of damaged cartilage by reducing the expression of matrix metalloproteases MMP-3, 7, 13, inhibit the secretion of NO, and promote the synthesis of collagen and proteoglycan in cartilage. Taken cumulatively, these results suggest that ultrasound may improve extracellular matrix production.

Additional benefits may be achieved by using surfactants in conjunction with ultrasound. This synergism is possibly due to the dual benefit of stratum corneum disruption by the surfactants along with the cavitation effect provided by ultrasound.

Notably, the use of harsh surfactants or high energy probes can irreversibly damage the skin losing its ability to stabilize or heal itself post treatment. The device of the present invention provides improved safety over ultrasound devices and methods which deliver ultrasound energy directionally perpendicular to the skin with (or without) formulations containing alcohol, surfactants and other emulsifiers, substantially reducing the amount of energy delivered under the skin.

Additionally, ultrasound is useful in breaking-down of melanin granules. Melanin present in skin helps in attenuating UV and visible radiation. The melanin is associated with such skin optical properties as light scattering; such skin optics aid in understanding skin health, physiology and pigmentation. Hyperpigmentation is a skin condition which is caused by excess production of melanin due to hormonal changes, excess sun exposure etc. To treat hyperpigmentation, typically topical treatments like alpha hydroxyl acids, retinoids, have been used as peels, masks or lotions to reduce pigmentation. Breaking-down melanin granules into smaller particles enables easier removal through skin exfoliation which can potentially modify the skin's optical properties and attenuate hyperpigmentation.

Without being limited by theory, the present inventors believe that by directing ultrasound wave to the skin surface at angles other than at 90° relative to the application surface, transducer frequency ranges of 20 kHz or (about 20 kHz) to 3000 kHz (or about 3000 kHz), optionally from 100 kHz (or about 100 kHz) to 1000 kHz (or about 1000 kHz), or optionally from 250 kHz (or about 250 kHz) to 750 kHz (or about 750 kHz) can be utilized to enhance or improve the above mentioned ultrasound skin benefits while preventing and/or reducing any negative, detrimental or otherwise harmful effects on a user's skin (where ultrasound application as occurred).

In certain embodiments, the ultrasound waves or energy projected/directed to the application surface (e.g., skin surface) at an angle $\ominus$ (as shown in FIG. 3) other than at, or less than, 90° relative to the application surface by the device and methods of the present invention generate an ultrasound pressure which is lower than, optionally at least a 5 fold lower than, optionally 10 fold lower than, optionally 15 fold lower than the ultrasound pressure generated by ultrasound waves or energy projected/directed to the application surface at an angle $\ominus$ of 90° (or perpendicular) relative to the application surface when measured, in each case, using the Ultrasound Pressure Measurement Test described below. The higher the ultrasound pressure under the skin, the more tissue damage occurs under the skin.

In certain embodiments, the device and methods of the present invention are used to improve skin penetration of benefit agents.

A topical composition useful for propagation of ultrasound waves to and from an ultrasound device is preferably used in conjunction with the ultrasound device to facilitate transmission of ultrasound energy between the device and the skin surface. The topical composition may take the form of a wide variety of water or water-based products that include, but are not limited to, conventional leave-on products (such as water, liquids, lotions, creams, gels, sticks, sprays, and ointments), skin cleansing products (such as liquid washes, solid bars, and wipes), hair products (such as shampoos, conditioners, sprays, and mousses), film-forming products (such as masks) and the like. These product types may contain any of several cosmetically- or pharmaceutically-acceptable carrier forms including, but not limited to solutions, suspensions, emulsions such as microemulsions and nanoemulsions, gels, and solids carrier forms. Other product forms can be formulated by those of ordinary skill in the art. In certain embodiments, the topical composition is substantially free of (or free of) air bubbles in order to ensure good ultrasound transmission. The topical composition can include or not include (i.e., be free of) an active benefit agent.

In certain embodiments, the topical composition further comprises an active benefit agent for topical administration to a subject (e.g., a human) in need of treatment for a condition or disease treatable by such active benefit agent, or to otherwise provide the therapeutic effect associated with the active benefit agent. Such therapeutic effects include, but are not limited to: antimicrobial effects (e.g., antibacterial, antifungal, antiviral, and anti-parasitic effects); anti-inflammation effects including effects in the superficial or deep tissues (e.g., reduce or elimination of soft tissue edema or redness); elimination or reduction of pain, itch or other sensory discomfort; regeneration or healing enhancement of hard tissues (e.g., enhancing growth rate of the nail or regrowth of hair loss due to alopecia) or increase soft tissue volume (e.g., increasing collagen or elastin in the skin or lips); increasing adipocyte metabolism or improving body appearance (e.g., effects on body contour or shape, and cellulite reduction); and increasing circulation of blood or lymphocytes. The topical composition (with or without the benefit agent, may be spread directly by the fingers and then the ultrasound may be applied by the devices according to the present invention for a period of time sufficient to provide targeted delivery of the benefit agent. The period of time may vary from about 5 seconds to about 1 minute, or optionally from about 20 seconds to about 40 seconds. Alternatively, the composition may be applied to one area of the skin and spread out through contact with devices according to the present invention and a spreading motion of the device.

In one embodiment, a composition contains a safe and effective amount of an active benefit agent, for example, from about 0.001 percent to about 20 percent, such as from about 0.01 percent to about 10 percent, by weight of the composition of the active benefit agent.

In one embodiment, the topical composition contains at least one benefit agent useful for the treatment of skin conditions (including scalp conditions). Examples of such skin conditions include, but are not limited to acne (e.g., blackheads and whiteheads), rosacea, nodule-cystic, and other microbial infections of the skin; visible signs of skin aging (e.g., wrinkles, sagging, sallowness, and age-spots); loose or lax skin, folliculitis and pseudo-folliculitis barbae; excess sebum (e.g., for sebum reduction or oily/shining skin appearance inhibition or control); pigmentation (e.g., for reduction of hyperpigmentation such as freckles, melasma, actinic and senile lentigines, age-spots, post-inflammatory hypermelanosis, Becker's naevus, and facial melanosis or enhancing the pigmentation of light skin); excess hair growth (e.g., skin on the leg), or insufficient hair growth (e.g., on the scalp, such as in hypotrichosis [e.g., the scalp condition alopecia]); dermatitis (e.g., atopic, contact, or seborrheic dermatitis), dark circles under the eye, stretch marks, cellulite, excessive sweating (e.g., hyperhidrosis), and/or psoriasis.

(a) Topical Anti-Acne/Anti-Rosacea Compositions

In one embodiment, the topical composition also contains an anti-acne and/or anti-rosacea active benefit agent. Examples of anti-acne and anti-rosacea active benefit agents include, but are not limited to: benzoyl peroxide; sulfur; retinoids such as tretinoin, isotretinoin, motretinide, adapalene, tazarotene, azelaic acid, and retinol; salicylic acid; resorcinol; sulfacetamide; urea; antibiotics such as tetracycline, clindamycin, metronidazole, and erythromycin; anti-inflammatory agents such as corticosteroids (e.g., hydrocortisone), ibuprofen, naproxen, and hetprofen; and imidazoles such as ketoconazole and elubiol; and salts and prodrugs and mixtures thereof. Other examples of anti-acne active benefit agents include essential oils, alpha-bisabolol, dipotassium glycyrrhizinate, camphor, β-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and synthetic phospholipids and natural phospholipids such as ARLASILK™ phospholipids CDM, SV, EFA, PLN, and GLA (commercially available from Croda, Edison, USA).

(b) Topical Anti-Aging Compositions

In one embodiment, the topical composition also contains an anti-aging active benefit agent. Examples of suitable anti-aging active benefit agents include, but are not limited to; cross-linked hyaluronic acid; retinoids; dimethylaminoethanol (DMAE), copper containing peptides, vitamins such as vitamin E, vitamin A (retinol and its derivatives, e.g., retinyl palmitate), vitamin C (ascorbic acid and its derivative, e.g., Ascorbic Acid 2-Glucoside/AA2G), and vitamin B (e.g., niacinamide, niacin) and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, and beta-phenylpyruvic acid; tetrahydroxypropyl ethylene-diamine, N,N,N',N'-Tetrakis(2-hydroxypropyl)ethylenediamine (THPED); and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts and prodrugs and mixtures thereof.

(c) Topical Depigmentation Compositions

In one embodiment, the topical composition contains a depigmentation active benefit agent. Examples of suitable depigmentation active benefit agents include, but are not limited to: soy extract; soy isoflavones; retinoids such as retinol; kojic acid; kojic dipalmitate; hydroquinone; arbutin; transexamic acid; vitamins such as niacinamide, niacin and vitamin C (ascorbic acid and AA2G; azelaic acid; linolenic acid and linoleic acid; placertia; licorice; and extracts such as chamomile, grape seeds and green tea; natural actives (e.g., Un-denatured soy, mulberry, paper mulberry (family Moraceae, *Broussonetia kazinoki×B. papyrifera*), isoflavones, feverfew, goji berry, milk thistle extract, amaranth oil, pomegrenate, yerbe mate, white lily flower extract, olive leaf extract, phloretin and mixtures thereof), and salts and prodrugs and mixtures thereof.

(d) Topical Antipsoriatic Compositions

In one embodiment, the topical composition contains an antipsoriatic active benefit agent. Examples of antipsoriatic active benefit agents (e.g., for use as a seborrheic dermatitis treatment) include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, sulfur, menthol, and pramoxine hydrochloride, and salts and prodrugs and mixtures thereof.

(e) Topical Hair Growth or Regrowth Actives

In one embodiment, the topical composition contains hair growth or hair regrowth active benefit agent for growing or thickening hair of the scalp, eye brow or eye lash, may be used to treat hair conditions (such as hypotrichosis) topically. Such hair growth/regrowth agents stimulate hair growth and/or prevent hair loss. Examples of hair growth or hair regrowth active benefit agents include, but are not limited to, potassium channel opener, ATP-sensitive potassium channel, minoxidil, diazoxide or phenytoin, 5α-reductase inhibitors, finasteride, dutasteride (e.g. Avodart), turosteride, bexlosteride, izonsteride, epristeride, epigallocatechin, 5α-reductase type 1 inhibitor, azelaic acid, and SKF 105, 111, ketoconazole, fluconazole, spironolactone, flutamide, diazoxide, 17-α-hydroxyprogesterone, 11-α-hydroxyprogesterone, RU58841, fluridil, or QLT-7704, an antiandrogen oligonucleotide, a prostaglandin F2α analogs, prostaglandin analogs, a prostaglandin, Latisse and Lumigan (RTM: Bimatoprost), Xalatan (RTM: Latanoprost), Travatan (RTM: Travoprost), tafluprost, unoprostone, Prostin F2 Alpha (RTM: dinoprost), (2S)-3-((1, 1'-biphenyl)-4-ylsulfonyl)-N—((R)-phenyl(2-pyridinyl)methyl)-1, 3-thiazolidine-2-carboxamide, BOL303259X, PF3187207, Hemabate (RTM: Carboprost), Keranique (RTM: Kopexil), calcium chloride, botilinum toxin A, adenosine, DoxoRx (RTM: Not defined), docetaxel, tacrolimus, GP11046, GP11511, LGD 1331, ICX-TRC, methanethiosulfonate-01 (MTS-01), NEOSH1O1, HYG-102440, HYG-410, HYG-420, HYG-430, HYG-440, spironolactone, cortexolone 17a-propionate, RK-023, abatacept, Viviscal (RTM: Natural dietary supplement), morrF, ASC-J9 (RTM: (3Z, 5E)-6-(3, 4-dimethoxyphenyl)-4-hydroxyhexa-3, 5-dien-2-one), NP-619, ammonium trichloro(dioxoethylene-o, o')tellurate, metron-F1, PSK 3841, targretin (RTM: Bexarotene), MedinGel (RTM: Biodegradable drug), PF3187207, BOL303259X, (2S)-3-((1, 1'-biphenyl)-4-ylsulfonyl)-N—((R)-phenyl(2-pyridinyl)methyl)-1, 3-thiazolidine-2-carboxamide, THG11331, PF-277343, PF-3004459, raptiva, caffeine, coffee, a herb (e.g. saw palmetto, glycine soja, *Panax ginseng, Castanea Sativa, Arnica Montana, Hedera Helix* and *Geranium maculatum*), triamcinolone acetonide, a topical irritant (e.g. anthralin) or sensitizer (e.g. squaric acid dibutyl ester or diphenyl cyclopropenone), clomipramine, unsaturated fatty acids (e.g. gamma linolenic acid), a fatty acid derivative, salts thereof and mixtures thereof.

(e) NonSteroidal Anti-Inflammatory Agents

In one embodiment, the topical composition contains certain analgesic active benefit agents and as such may be prepared for topical treatment of pain, such as pain at or from the back, shoulder, joints, muscle sore/pain, menstrual cramps, or pain from cold sore or canker sore. Such benefit agents to relieve pain include, but are not limited to, Non-Steroidal Anti-Inflammatory Drugs (NSAIDs) such as ibuprofen, naproxen, salicylic acid, ketoprofen, and diclofenac and pharmaceutically acceptable salts thereof. Other topical analgesic active benefit agents for treating pain and itch include, but are not limited to, methyl salicylate, menthol, trolamine salicylate, capsaicin, lidocaine, benzocaine, pramoxine hydrochloride, and hydrocortisone.

(f) Other Topical Ingredients

In one embodiment, the topical composition contains a plant extract as the active benefit agent. Examples of plant extracts include, but are not limited to, feverfew, soy, glycine soja, oatmeal, what, aloe vera, cranberry, witch-hazel, alnus, arnica, artemisia capillaris, asiasarum root, birch, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural isoflavonoids, soy isoflavones, and natural essential oils.

In certain embodiments, any of the above described active benefit agents may be used in combination.

In certain embodiments, the topical compositions of the present invention also include sebum miscible compounds for improving transport of the active benefit agent through sebum and/or aiding in the cleansing of hair follicles. Suitable sebum miscible compound include compounds selected from $C_{10}$ to $C_{35}$, (optionally $C_{10}$-$C_{22}$) alkyl lactates such as the following $C_{10}$-$C_{18}$ alkyl lactates: cetyl lactate, myristyl lactate, glyceryl stearate lactate or $C_{12}$-$C_{15}$ alkyl lactate and the like and mixtures thereof; volatile silicones such as Dow Corning—345 fluid, DC 200 fluid, and those described in U.S. Pat. No. 5,084,577, fatty acid esters (e.g. octyl isononanoate, octyl palmitate, Isodecyl oleate, propylene dicaprylate), liquid fatty alcohols (e.g. oleyl alcohol), aromatic alcohols such as phenyl alcohols with chemical structures of $C_6H_5$—R(OH) where R is an aliphatic radical, such as benzyl alcohol and phenethyl alcohol; aromatic glycol ethers such as ethylene glycol phenyl ether; propylene or butylene oxide-based glycol ethers such as propylene glycol methyl ether and those disclosed in U.S. Pat. No. 5,133,967, incorporated herein by reference in its entirety; fatty acids, polyunsaturated fatty acids such as linoleic acid, linolenic acid, stearidonic acid, plant, fruit, or marine derived extracts rich in essential fatty acid or polyunsaturated fatty acids such as but not limited to *Vaccinium myrtillus* (bilberry) seed oil, *Vaccinium macrocarpon* (cranberry) seed oil, *Vaccinium vitis-idaea* (lingonberry) seed oil, *Rubus idaeus* (raspberry) seed oil, *Rubus chamaemorus* (cloudberry) seed oil, *Ribes nigrum* (black currant) seed oil, *Hippophae rhamnoides* (sea buckthorn) seed oil, *Echium plantagineum* (echium) seed oil, *Hordeum vulgare* (barley) seed oil, *Betula alba* bud extract, saw palmetto extract, borage oil, evening primrose oil, soy oil; cetyl ocenate; isostearyl benzoate; pentaerythiol teraoctenate; isostearyl benzoate; and combinations thereof. In certain embodiments, the sebum miscible compound of the present invention is selected from the group consisting of $C_{12}$-$C_{15}$ alkyl lactates, myristyl lactate, cetyl lactate, glyceryl stearate lactate, ethylene glycol phenyl ether; propylene or butylene oxide-based glycol ethers, volatile silicones and mixtures thereof. In certain embodiments, the sebum miscible compound of the present invention is selected from the group consisting of $C_{12}$-$C_{15}$ alkyl lactates, cetyl lactate, myristyl lactate or mixtures thereof.

In certain embodiments, the sebum miscible compound is present in the topical composition in an amount of from 0.5% (or about 0.5%) to 5% (or about 5%), optionally, from 1.0% (or about 1.0%) to 4% (or about 4%), or, optionally, from 1.5% (or about 1.5%) to 3% (or about 3%), by weight of the composition.

In certain embodiments, the sebum miscible compound is incorporated in the ultrasound wave propagating topical composition without further incorporation of an active benefit agent for purposes of cleansing, or aiding in the cleansing, of skin pores, hair follicles or other openings/crevasses in the skin. Alternatively, the sebum miscible compound is incorporated in the ultrasound wave propagating topical composition with an active benefit agent for purposes of cleansing the skin openings and improving transport of the active benefit agent to (and through) skin surface.

In an embodiment of the present invention, the ratio of the active benefit agent to the sebum miscible compound is from 10:1 (or about 10:1) to 1:1 (or about 1:1), optionally 5:1 (or about 5:1) to 1:1 (or about 1:1), optionally 3:1 (or about 3:1) to 1:1 (or about 1:1), or optionally 2:1 (or about 2:1).

In one embodiment, the topical composition contains one or more buffering agents such as citrate buffer, phosphate buffer, lactate buffer, gluconate buffer, or gelling agent, thickener, or polymer.

In one embodiment, the composition or product contains a fragrance effective for reducing stress, calming, and/or affecting sleep such as lavender and chamomile.

In one embodiment, the composition is applied into wounds to provide healing enhancement or scar prevention. Wounds or lesions that may be treated include, but are not limited to acute wounds as well as chronic wounds including diabetic ulcer, venus ulcer, and pressure sores.

The composition may include an antifungal drug or an antibiotic as the active benefit agent. Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. In one embodiment, the antifungal drug is an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline-10 hydrochloride and tetrachcycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs.

Examples of antimicrobials that may be useful in the composition include but are not limited to salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl and benzethonium chloride. Other antimicrobials include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. In one embodiment, the alcohol is at a low concentration (e.g., less than about 10% by weight of the carrier, such as less than 5% by weight of the carrier) so that it does not cause undue drying of the barrier membrane.

Examples of anti-viral agents that may be useful as the active benefit agent in the topical composition for such viral infections as herpes and hepatitis, include, but are not limited to, imiquimod and its derivatives, podofilox, podophyllin, interferon alpha, acyclovir, famcyclovir, valcyclovir, reticulos and cidofovir, and salts and prodrugs thereof.

Examples of anti-inflammatory agents that may also be useful as the active benefit agent in the topical composition include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. In one embodiment, the steroidal anti-inflammatory for use in the present invention is hydrocortisone. A second class of anti-inflammatory agents which is useful in the compositions of the present invention includes the nonsteroidal anti-inflammatory agents.

Examples of wound healing enhancing agents that may be useful as the active benefit agent in the topical composition include platelet rich plasma (i.e., plasma having a platelet concentration of at least 1 million per microliter), recombinant human platelet-derived growth factor (PDGF) and other growth factors, ketanserin, iloprost, prostaglandin E1 and hyaluronic acid, scar reducing agents such as mannose-6-phosphate, analgesic agents, anesthetics, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs. In certain embodiments of the present invention, the platelet rich plasma, recombinant human platelet-derived growth factor (PDGF) and other growth factors are also useful as hair growth or regrowth agents.

In one embodiment, the composition is used, with or without other antifungal active agents, to treat or prevent fungal infections (e.g., dermatophytes such as *Trichophyton mentagrophytes*), including, but not limited to, onychomycosis, sporotrichosis, tinea unguium, tinea pedis (athlete's foot), tinea cruris (jock itch), tinea corporis (ringworm), tinea capitis, tinea versicolor, and candida yeast infection-related diseases (e.g., *Candida albicans*) such as diaper rash, oral thrush, cutaneous and vaginal candidiasis, genital rashes, Malassezia furfur infection-related diseases such as Pityriasis versicolor, Pityriasis folliculitis, seborrhoeic dermatitis, and dandruff.

In another embodiment, the topical composition is used, with or without other antibacterial active agents, to treat and prevent bacterial infections, including, but not limited to, acne, cellulitis, erysipelas, impetigo, folliculitis, and furuncles and carbuncles, as well as acute wounds and chronic wounds (venous ulcers, diabetic ulcers and pressure ulcers).

In another embodiment, the topical composition is used, with or without other antiviral active agents, to treat and prevent viral infections of the skin including, but not limited to, molluscum contagiosum and warts.

In another embodiment, the topical composition is used, with or without other antiparasitic active agents, to treat and prevent parasitic infections, including, but not limited to, hookworm infection, lice, scabies, sea bathers' eruption and swimmer's itch.

The composition can also be used to stimulate nail growth, enhance nail strength, and reduce nail infection or discoloration. The composition can be incorporated into compositions for the treatment of onychomychosis with active benefit agents such as, but not limited to miconazole, econazole, ketoconazole, sertaconazole, itraconazole, fluconazole, voricoriazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. The composition can be incorporated into compositions for improving the look and feel of nails with ingredients such as, but not limited to: biotin, calcium panthotenate, tocopheryl acetate, panthenol, phytantriol, cholecalciferol, calcium chloride, Aloe Barbadensis (Leaf Juice), silk protein, soy protein, hydrogen peroxide, carbamide peroxide, green tea extract, acetylcysteine and cysteine.

Method of Practicing

More specifically, in certain embodiments, the topical compositions containing the active benefit agents of the present invention are applied to the affected areas of the skin or scalp (i.e., areas in need of treatment from the active benefit agents) followed by application ultrasound at the area of application of the topical composition. The ultrasound device is calibrated to provide acoustic energy at a frequency ranging from about 20 kHz to about 3000 kHz the head of the ultrasound comprising the transducer is positioned over the area of application such the ultrasound waves are directed towards the affected area at an angle $\Theta$ other than at 90° (perpendicular) relative to the surface of the affected area (or as further described herein above). Also, a topical composition (with or without an active benefit agent) is usually applied between the subject's skin for efficient propagation of ultrasound waves to and from the transducer of the ultrasound device. The duration of each application of ultrasound acoustic energy ranges from about 5 seconds to about 1 minute. The above method is repeated for at least two consecutive applications, optionally, at least 2 consecutive applications at a frequency of at least once daily.

In certain embodiments, the ultrasound devise can be configured and/or sized for stationary application on the skin such as by means of a "cap", "band", "wrap with attachable ends" or "patch".

Several examples are set forth below to further illustrate the nature of the invention and the manner of carrying it out. However, the invention should not be considered as being limited to the details thereof.

EXAMPLES

Examples are set forth below to further illustrate the nature of the invention and the manner of carrying it out. However, the invention should not be considered as being limited to the details thereof.

Example 1

Ibuprofen Gel Preparation

A topical ibuprofen gel composition was prepared with the ingredients in Table 1 below, following the procedures described below.

TABLE 1

| No. | Ingredients | Source of Ingredient | Ibuprofen Gel Formulation (weight %) |
|---|---|---|---|
| 1 | Ethyl Alcohol | | 20 |
| 2 | Ibuprofen, USP | | 5 |
| 3 | Propylene glycol | | 2 |
| 4 | Butylated hydroxytoluene (BHT) | | 0.1 |
| 5 | Water, USP | | 69.1 |
| 6 | Carbopol (Ultrez 30) | | 1 |
| 7 | Triethylamine | | 2.8 |
| | Total | | 100 |

Procedure: Ingredients No. 1-4 were weighed into a container and mixed until uniform. Ingredients Nos. 5 and 6 were weighed and added, then mixed to form a uniform suspension. Ingredient 7 was added under mixing until a uniform clear gel was formed with a final gel pH of 6.8.

Example 2

The experimental setup to run sonophoresis (ultrasound) studies with Franz cell diffusion cells consisted of a custom-built universal generator capable of driving ultrasonic transducers in the 20 kHz-2 MHz range with electronic power up to 60 W (Voltage+/−30V, Current: 2 A, duty cycle 50%) with a square waveform. The real power delivered to the transducer depended on the specific experimental conditions and is specified for each experiment. The driving waveform was delivered to the transducer through a coaxial cable having a BNC connector at one end and a custom non-coaxial connector at the transducer end.

The transducer was piezoelectric and had either a disk shaped form (either 20 or 25 mm in diameter) or a rectangular shape 10×20 mm$^2$). The thickness of the transducer depended on its fundamental frequency being inversely proportional with it. In order to prevent the liquid or the gel from perturbing the electrical connection, each transducer was encapsulated in a plastic case leaving only one side of the transducer exposed to the topical composition. The case was made out of a rigid plastic and the transducers were sealed with silicone adhesive to enable them to oscilalte more or less freely. The case also enabled the electrical connections to be isolated from the topical composition.

For sonophoresis experiments where the ultrasonic wave energy was delivered perpendicular to the skin, disk-shaped transducers were used in the encapsulation setup described above. For the angled ultrasound application the case encapsulating the ultrasonic transducer was assembled in a hinged configuration, enabling angles between 15 and 90 degrees (perpendicular). Note: an angle of 0 degrees would send the ultrasonic wave parallel with the skin surface.

In order to have a tight control over the experimental conditions the following sequence was used in all the studies:

1. Test the impedance/frequency parameters of the encapsulated transducer with the help of an Agilent 4294A impedance tester—which is the tester of choice for any ultrasonic material and device in the industry and research. Parameters were recorded and traced during the entire life of the transducer being measured always before and after a study was performed.

The parameters of interest were: Series resonance value—it should be the smallest possible for the given transducer; phase angle below and after the series resistance—it should be the closest possible to −90 degrees before and +90 degrees above the series resonance frequency, and no parasitic resonances in the capture band of the driver (the driver is capable to adjust its frequency to the specific study parameters and needs "smooth" phase transitions).

2. Test the ultrasonic energy delivered to a specified amount of water through the acoustic pressure method. The test setup used a plastic dish placed on a scale in which the transducer was lowered in the water keeping a fixed distance from the bottom and being held at that fixed height by an external support (not in contact with the scale). The transducer was driven with the universal driver at the resonance frequency and the additional weight produced by the acoustic pressure was recorded in correlation with the electrical power. The method is a qualitative one meant to characterize if the transducer works repeatedly.

3. Study with the diffusion Franz cells at the specified power and test conditions.

4. Repeat the test with the ultrasonic energy—check against the initial values.

5. Repeat the test with the impedance tester—check against the initial values.

In Vitro Skin Permeation Studies

Procedures of Ibuprofen Skin Permeation Studies with Ultrasound or without Ultrasound:

In vitro skin permeation studies on 5% Ibuprofen gel compositions without ultrasound (passive diffusion), or facilitated by the application of ultrasound (sonophoresis), through human cadaver skin were performed as follows:

A skin penetration study evaluated the penetration of ibuprofen through the human skin for the inventive sample prepared as disclosed in Example 1. A commercial ibuprofen gel product, IBULEVE Ibuprofen Gel (by DDD ltd, Watford, Herts, WD18 7JJ, UK) was used as a benchmark, which contains 5% W/W ibuprofen, also IMS (Industrial Methylated Spirits), carbomer, propylene glycol, diethylamine and purified water according to the product label on its package. A well-known Franz diffusion cell method (taught in US20020006418 A1 which is hereby incorporated by reference) was used. Franz cells had a diameter of 3.0 cm, and surface area 7.07 cm$^2$ for the donor cell, and a volume of receptor compartment of 25 ml. A magnetic stirrer bar was added in the donor compartment. The liquid receptor was filled with Phosphate-buffered saline (PBS) solution. Air bubbles in the donor compartment were removed. The system was thermostated at 37° C. above a magnetic stirrer to ensure the homogeneity of the liquid receptor during the experiment. A human cadaver skin sample from a commercial tissue bank (Ohio Valley Tissue and Skin Center, Cincinnati, Ohio, dermatomed to approximately 0.4 mm) was cut to fit the glass diffusion cell and the skin was mounted on the Franz cell.

For the diffusion cells designated to be tested for passive diffusion, a test gel sample of 0.2 ml was applied on the skin surface. For the diffusion cells designated to test for sonophoresis, additional test sample (2-5 ml) was added in order to assure the entire, or at least a large portion, of the ultrasonic transducer tip was immersed by the test gel during the ultrasound treatment. The excess gel was promptly removed from the donor cell after the ultrasound treatment so that the remaining test gel was approximately 0.2 ml.

Ultrasound treatments were carried out with the following test conditions:
a) Conventional ultrasound treatment with 90 degree angle (°) between the ultrasound direction and the skin surface;
b) Angled Ultrasound treatment with less than 90 degree angle between the ultrasound direction and the skin surface.

Samples were collected from the receptor compartment at pre-determined time points, e.g., 0, 0.5, 1, 2, 4, 6 and up to 24 hours. At the end of the study, samples collected from the receptor compartments of the Franz cells were analyzed for ibuprofen levels with a High-performance liquid chromatography (HPLC) system and the amount of ibuprofen that penetrated across the skin layer was calculated.

Ibuprofen Skin Permeation Results:

The results are shown in Tables 2-4. The final average of the calculated ibuprofen levels in different skin layers are reported in micrograms (µg) for 3 different replicates.

Table 2 shows the ibuprofen skin permeation results from Study 1, in which ultrasound treatment (UT) was applied, at a signal power of 3 W, in such a way that the ultrasound transducer delivered the ultrasound energy at a frequency of 700 kHz to the skin surface with a 45 degree angle for one group of three diffusion cells. For comparison purpose, another group of three diffusion cells was run with passive diffusion without any ultrasound treatment.

TABLE 2

| | Ibuprofen Diffusion (µg) | | |
|---|---|---|---|
| Time (hr) | UT (Diffusion with Gel 1 and 45° Sonophoresis) | Non-UT$_{Gel1}$ (Passive Diffusion with Gel 1) | Non-UT$_{Gel2}$ (Passive Diffusion with Gel 2, IBULEVE) |
| 0.5 | 653 ± 949 | 25 ± 20 | 1 * |
| 1 | 1073 ± 1321 | 85 ± 29 | 16 ± 4 |
| 2 | 1918 ± 1945 | 254 ± 21 | 71 ± 17 |
| 3 | 2744 ± 2652 | 425 ± 17 | 134 ± 36 |
| 4 | 3253 ± 3009 | 563 ± 34 | 193 ± 49 |
| 6 | 4017 ± 3377 | 927 ± 231 | 333 ± 66 |
| 20 | 6450 ± 4294 | 2185 ± 776 | 1237 ± 70 |
| 22 | 6511 ± 4235 | 2224 ± 654 | 1372 ± 95 |
| 24 | 6833 ± 4147 | 2483 ± 891 | 1472 ± 67 |
| | UT$_{45°}$/Non-UT$_{Gel1}$ | | UT$_{45°}$/Non-UT$_{Gel2}$ |
| 6 hr | 4.3 | | 12.1 |
| 24 hr | 2.8 | | 4.6 |

The results in Table 2 indicate that 45 degree angled sonophoresis significantly enhanced ibuprofen permeation through the human skin to reach the receptor compartment. For example, the ibuprofen skin permeation enhancement factors for ibuprofen traveled across the skin from the 45 degree UT sonophoresis from the ibuprofen gel from Example 1, compared to that without ultrasound from the same ibuprofen gel were approximately 4.3 fold at the $6^{th}$ hour and 2.8 fold at the $24^{th}$ hour, respectively. When compared to ibuprofen passive diffusion from the commercial ibuprofen gel, IBULVE, the ibuprofen skin permeation enhancement factors were 12.1 fold at the $6^{th}$ hour and 4.6 fold at the $24^{th}$ hour, respectively.

Table 3 shows the ibuprofen skin permeation results from Study 2, in which ultrasound treatment (UT) was applied, at a signal power of 3 W, in such a way that the ultrasound transducer delivered the ultrasound energy at frequency of 700 kHz to the skin surface with a 60 degree angle for one group of three diffusion cells (middle column or column 2). For comparison purpose, another group of three diffusion cells was run with passive diffusion without any ultrasound treatment (the last column or column 3). The first column (column 1) was intended for ultrasound treatment also. However, it was found out that the ultrasound transducer did not work during ultrasound treatment because a test on the ultrasound transducer after the ultrasound treatment revealed that there was no ultrasound pressure coming out of the transducer tip, therefore, this group of diffusion cells was in fact passive diffusion without any ultrasound treatment, just like the test condition for the last column (column 3).

TABLE 3

| | Ibuprofen Diffusion (µg) | | |
|---|---|---|---|
| Time (hr) | No-UT (due to a failed ultrasonic transducer) | UT$_{60°}$ (Diffusion with Gel 1 and 60° Sonophoresis) | Non-UT$_{Gel1}$ (Passive Diffusion with Gel 1) |
| 0.5 | 14 ± 12 | 128 ± 154 | 4 ± 4 |
| 1 | 81 ± 29 | 358 ± 186 | 39 ± 8 |
| 2 | 285 ± 56 | 980 ± 313 | 184 ± 16 |
| 4 | 633 ± 145 | 1802 ± 765 | 496 ± 27 |
| 6 | 1078 ± 281 | 2687 ± 1266 | 939 ± 17 |
| 24 | 2374 ± 704 | 5506 ± 3307 | 2736 ± 215 |
| | | UT$_{60°}$/Non-UT$_{Gel1}$ | |
| 6 hr | | 2.9 | |
| 24 hr | | 2.0 | |

The results in Table 3 indicate that without any ultrasound treatment, ibuprofen passive diffusion resulted in similar ibuprofen permeated across the skin and reached the receptor compartment as one compares the results in columns 1 and 3. In contrast, 60 degree angled sonophoresis significantly enhanced ibuprofen permeation through the human skin to reach the receptor compartment. The permeation enhancement factors for ibuprofen from the 60 degree UT sonophoresis to that without ultrasound (column 3) at the $6^{th}$ hour and the $24^{th}$ hour were approximately 2.9 fold at the $6^{th}$ hour and 2.0 fold at the $24^{th}$ hour.

Table 4 shows the ibuprofen skin permeation results from Study 3, in which ultrasound treatment (UT) was applied, at a signal power of 3 W, in such a way that the ultrasound transducer delivered the ultrasound energy at a frequency of 700 kHz to the skin surface with a 15 degree angle for one group of three diffusion cells (column 1), and with a 90 degree angle for another group of three diffusion cells, which is how ultrasound treatment was applied in most sonophoresis studies. For comparison purpose, another group of three diffusion cells was run with passive diffusion without any ultrasound treatment (the last column or column 3).

TABLE 4

| | Ibuprofen Diffusion (µg) | | |
|---|---|---|---|
| Time (hr) | $UT_{15°}$ (Diffusion with Gel 1 and 15° Sonophoresis) | $UT_{90°}$ (Diffusion with Gel 1 and 90° Sonophoresis) | Non-$UT_{Gel1}$ (Passive Diffusion with Gel 1) |
| 0.5 | 173 ± 112 | 43 ± 34 | 6 ± 4 |
| 1 | 654 ± 457 | 410 ± 169 | 31 ± 39 |
| 2 | 2589 ± 1610 | 2086 ± 1008 | 477 ± 561 |
| 4 | 6512 ± 3688 | 5379 ± 2540 | 1931 ± 1910 |
| 6 | 11058 ± 6446 | 8379 ± 4147 | 3640 ± 3518 |
| 24 | 54073 ± 35886 | 35725 ± 12187 | 18051 ± 18485 |
| | $UT_{15°}$/Non-$UT_{Gel1}$ | $UT_{90°}$/Non-$UT_{Gel1}$ | |
| 6 hr | 3.0 | 2.3 | — |
| 24 hr | 3.0 | 2.0 | — |

The results in Table 4 indicate that both 15 degree (column 1) and 90 degree ultrasound (column 2) treatments significantly enhanced ibuprofen permeation through the human skin, as opposed that without ultrasound treatment (column 3). The permeation enhancement factors for 15 degree UT sonophoresis to that without ultrasound treatment (column 3) at the $6^{th}$ hour and the $24^{th}$ hour were approximately 3.0 fold at the $6^{th}$ hour and the $24^{th}$ hour; and the enhancement factors for 90 degree UT sonophoresis (column 3) to that without ultrasound (column 3) at the $6^{th}$ hour and the $24^{th}$ hour were approximately 2.3 fold at the $6^{th}$ hour and 2.0 fold at the $24^{th}$ hour. It was a surprise that the angled ultrasound treatment of 15 degrees could lead to drug skin permeation enhancement similar, or perhaps even better, to that from 90 degree ultrasound treatment used conventionally, in addition to the aforementioned significant safety benefits of eliminating the deep tissues from unintended ultrasound exposure.

Ultrasound Pressure Measurement Test.

Figure 4A:
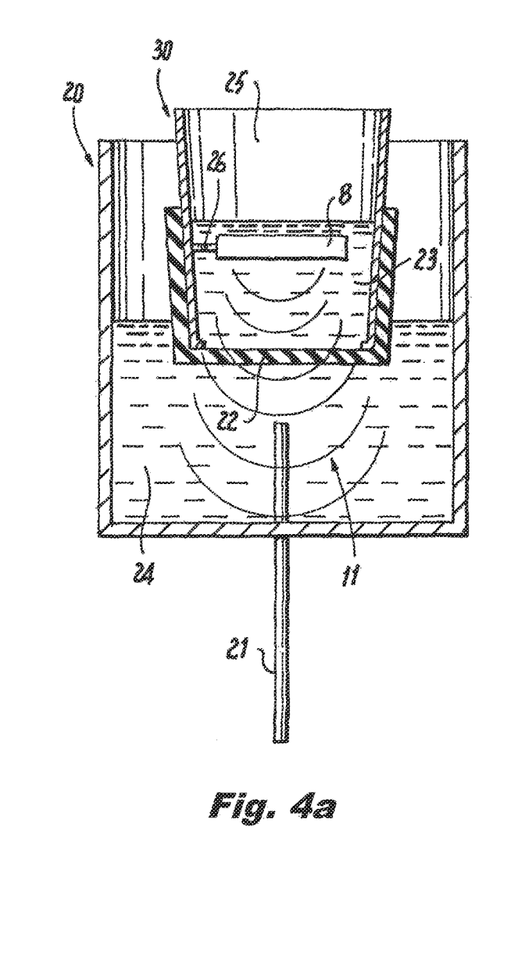
FIG. 4a. depicts the setup/apparatus for the Ultrasound Pressure Measurement Test described in the Specification hereof with the transducer positioned such that the propagation/direction of the ultrasound wave is perpendicular silicone skin 22.
Figure 4B:
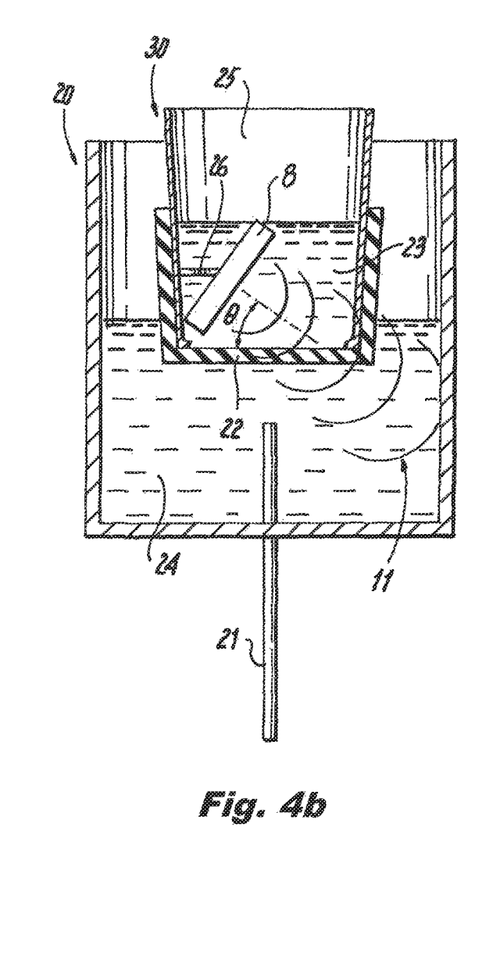
FIG. 4b. depicts the setup/apparatus for the Ultrasound Pressure Measurement Test described in the Specification hereof with the transducer positioned such that the propagation/direction of the ultrasound wave forms an angle $\ominus$ of about 15° relative to the planar surface of the silicone skin 22.

To demonstrate the improved safety of orienting the transducer such that ultrasound waves are directed to the application site(s) (i.e., skin surface) at angles ⊖ (as described herein), an in vitro, Ultrasound Pressure Measurement Test was performed. The Ultrasound Pressure Measurement Test determines the ultrasonic pressure generated by the device or methods of the present invention using an Onda hydrophone calibrated for 30 kHz-10 MHz range when delivering the ultrasonic energy at variable angles ranging from 90 (perpendicular) to 15 degrees. The Ultrasound Pressure Measurement Test uses the setup illustrated in FIGS. 4a and 4b. FIGS. 4a and 4b show outer vessel 20 in which an inner vessel 30 having a bottom formed from silicone skin 22 (manufactured by Skindaver/Florida) is positioned. Water is added to each of vessels 20 and 30 as illustrated in FIGS. 4a and 4b to form topical region 23 (i.e., region between transducer 8 and the silicone skin 22) and a region "below [or underneath] the skin" 24 (i.e., below the silicone skin 22). Thus formed, the region "below the skin" 24 simulates the tissue region under the natural skin of living creatures. The topical region 23 simulates the topical composition used in conjunction with ultrasound generating transducer 8. A hydrophone 21 (Onda HNR-1000 connected through an AH-1100 amplifier to a Tektronix oscilloscope) is positioned in the region "below the skin" 24 to measure the voltage generated by the ultrasound waves projected from transducer 8 through silicone skin 22; the measured voltage is directly proportional to the acoustic pressure of the generated by ultrasound waves at region "below the skin" 24.

The ultrasonic energy is applied at 714 kHz with a signal power of 3 W (40V peak to peak at 0.15 A). Using the setup of FIGS. 4a and 4b, the ultrasonic energy is first applied to the silicone skin 22 from a transducer 8 which is positioned by positioning element 26 so that the ultrasonic wave is directed perpendicular to the silicone skin 22 by positioning element 26 as in FIG. 4a. Using the setup of FIG. 4b, the ultrasonic energy is again applied to the silicone skin 22 from a transducer 8 which is positioned by positioning element 26 so that the ultrasonic energy wave propagation direction forms an angle ⊖ of about 15° relative to the planar surface of the silicone skin as in FIG. 4b. The transducer 8 oriented such that the ultrasound waves are perpendicular to the silicone s generated an amplitude of 10V. The transducer 8 oriented such that the ultrasound waves are directed towards the silicone skin 22 at angle ⊖ of about 15° relative to the planar surface of the silicone skin (i.e., as in the case of angle ⊖ as illustrated in FIG. 3) generated an amplitude of only 0.9V. The roughly 10 fold reduction in amplitude voltage correlates to a roughly 10 fold reduction in ultrasonic pressure in the tissue under the skin, suggesting the increased tissue safety of the angled ultrasound wave projection (towards skin surface) relative to perpendicular ultrasound wave projection (towards skin surface).

Mice Hair Growth Study

Experimental Design

Duration of Study

The in-life phase portion of this study was 60 days in duration. The in-life phase began with the start of clinical observations Day −3 and ended with necropsies on Day 56. The day of the first dose was designated as Day 0.

Group Allocation

Mice were allocated to 11 groups as they were brought into the facility and placed in cages. Each group was composed of 5 mice. The last five numeric animals were deemed replacement animals and enrolled as needed on Day 0.

Test Article and Route of Administration

For dermal administration of the Test Gel, the mice were shaved on Day 0 prior to dose application. The mouse was manually restrained by a technician, a syringe or pipette was used to draw the dose of the Test Gel, and Test Gel was applied to the back of the animal.

Frequency and Duration of Dosing

The Test Gel was administered once daily for 56 days. The times of dose administration were recorded. Due to the variable nature of dermal application procedures and due to the need to perform various evaluations before dosing, the time of dosing of each animal varied daily.

Observations, Measurements, and Specimens

Physical Examinations

Prior to study start, each animal was confirmed to be healthy by a medical record completed by a veterinarian, a certified veterinary technician, or an approved research technician. The criteria of health included the absence of abnormal clinical signs during the 3 days prior to initial dosing and a normal physical exam. All study animals were in good health.

Clinical Observations

Animals were observed at least once daily 3 days prior to initial dosing (pre-study for health assessment). The last clinical observation was the morning of Day 56 before euthanasia. All observations were recorded at the time of occurrence. Live phase assessment included but were not limited to assessment of activity, posture, respiration, hydration status, and overall body condition.

Dose Groups, Concentration, and Application Procedures

The dosing solutions are outlined in Table 5 below:

TABLE 5

Design of Study Groups for Test Gels (TG)

| Test Article | Amount applied (mL) | Application procedures | Days Administered |
|---|---|---|---|
| Group 1 - Untreated | 0 | None | None |
| Group 2 - Test Gel 1 | 0.4 | Rub in Test Gel onto dorsal skin for 30 strokes (about 30 seconds) with a gentle pressure | 0-55 |
| Group 3 - Test Gel 2 | 0.4 | 1) Rub in Test Gel onto dorsal skin for 30 strokes (about 30 seconds) | 0-55 |
| Group 4 - Test Gel 1 with UT1 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 5 - Test Gel 2 with UT1 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 6 - Test Gel 1 with UT2 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 7 - Test Gel 2 with UT2 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 8 - Test Gel 1 with UT3 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 9 - Test Gel 2 with UT3 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 10 - Test Gel 1 with UT4 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |
| Group 11 - Test Gel 2 with UT4 | 0.4 | 1) Apply Test Gel onto dorsal skin uniformly 2) Apply Ultrasound Treatment on dorsal skin 3 times/week, by pressing the ultrasound device head onto Test Gel layer on the mouse skin in a circulation motions 30 times (about 30 seconds) to cover the entire dorsal skin | 0-55 |

\* For ultrasound treatment, the head of the device (ultrasound transducer) should be pressed against the mouse skin over the gel formulation layer without any air gap, and be moved in a circulation motion, and this procedure is repeated to cover the entire dorsal skin of the animal. For groups 3 through 11, animals will be treated with the ultrasound device on Day 0 and 3 for week one dosing and then on a Monday-Wednesday-Friday schedule thereafter. On days when no ultrasound treatment is indicated, only Test Gels will be applied to the treated skin area.

Test Groups
1 Untreated (Negative Control)
2 Placebo gel daily (Test Gel 1)
3% Minoxidil Gel daily (Test Gel 2)
4 UT1+Placebo Gel (Test Gel 1+UT1, 3×/week)
5 UT1+5% Minoxidil Gel (Test Gel 2+UT1, 3×/week)
6 UT2+Placebo Gel (Test Gel 1+UT2, 3×/week)
7 UT2+5% Minoxidil Gel (Test Gel 2+UT2, 3×/week)
8 UT3+Placebo Gel (Test Gel 1+UT3, 3×/week)
9 UT3+5% Minoxidil Gel (Test Gel 2+UT3, 3×/week)
10 UT4+Placebo Gel (Test Gel 1+UT4, 3×/week)
11 UT4+5% Minoxidil Gel (Test Gel 2+UT4, 3×/week)

Ultrasound Treatments (UT) 1-4 were adjusted by changing the device setting and/or the treatment tip to produce the following parameters: (i. transducer frequency, ii. ultrasound wave projection angle, and iii. time of ultrasound application):

UT1—Ultrasound Treatment 1 (50 kHz, 90 Degree, 30 Seconds)
UT2—Ultrasound Treatment 2 (50 kHz, 15 Degree, 30 Seconds)
UT3—Ultrasound Treatment 3 (700 kHz, 90 Degree, 30 Seconds)
UT4—Ultrasound Treatment 4 (700 kHz, 15 Degree, 30 Seconds)

The 5% minoxidil gel used as Test Gel 2 in the above Test Groups was prepared by mixing the ingredients shown in Table 6 using conventional mixing technology. The 1% Klucel-thickened commercial 5% minoxidil solution gel used as Test Gel 1 was prepared by mixing the Klucel (hydroxypropylcellulose) into a commercially available Walgreen's 5% Minoxidil Topical Solution using conventional mixing technology to form a 1% Klucel minoxidil gel.

TABLE 6

| Chemical Name | Trade Name | % (w/w) |
|---|---|---|
| Ethyl Alcohol | SDA Alcohol 40B 190 Proof | 21.00 |
| Pentylene Glycol | Hydrolite 5 supplied by Symrise, Teterboro, NJ | 4.00 |
| Glycerin | Glycerin USP | 12.00 |
| Citric Acid | Citric Acid | 0.20 |
| Lactic Acid | Purac HiPure 90 | 3.00 |
| Minoxidil | Minoxidil USP | 5.00 |
| Butylated Hydroxytoluene | BHT | 0.10 |
| Water | Purified Water | 44.20 |
| Sodium Pyruvate | Sodium Pyruvate | 1.00 |
| Polyquaternium-37 | Cosmedia Ultragel 300 supplied by BASF, Florham Park, N.J. | 2.50 |
| Steareth-2 | Brij S2 | 1.50 |
| Steareth-10 | Brij S10 supplied by Croda, Edison, NJ | 2.00 |
| Cetyl Lactate | Ceraphyl 28 | 3.00 |
| Tocopheryl Acetate | dl-a Tocopheryl Acetate | 0.50 |
| pH = 5.69 | | 100.00 |

Table 7 is the average of the degree of terminal hair coverage for the 5 mice in each of Groups 1-11 based on images taken at different time points. Visual observation of images taken at week 0 (day that mice were shaved) demonstrated that, at this stage of the study, all the mice of test groups had all terminal hair removed.

TABLE 7

AVERAGE MOUSE HAIR COVERAGE SCORE

| Groups | Day 0 | Day 17 | Day 24 | Day 31 | Day 38 | Day 45 | Day 52 |
|---|---|---|---|---|---|---|---|
| 1 (Untreated) | 0 | 0 | 0 | 0 | 0.2 | 1 | 1.2 |
| 2 (Test Gel 1) | 0 | 1.4 | 3.8 | 4.2 | 4.4 | 4.8 | 5 |
| 3 (Test Gel 2) | 0 | 0 | 3.4 | 4.6 | 4.8 | 5 | 5 |
| 4 (Test Gel 1 + UT1) | 0 | 1.2 | 3.2 | 4.2 | 4.4 | 5 | 5 |
| 5 (Test Gel 2 + UT1) | 0 | 0 | 2.8 | 4.4 | 4.8 | 5 | 5 |
| 6 (Test Gel 1 + UT2) | 0 | 0 | 0.6 | 3 | 4 | 4.8 | 5 |
| 7 (Test Gel 2 + UT2) | 0 | 0 | 1.8 | 2.8 | 4 | 4.4 | 4.8 |
| 8 (Test Gel 1 + UT3) | 0 | 0.6 | 1.6 | 3.4 | 3 | 4.2 | 4.6 |
| 9 (Test Gel 2 + UT3) | 0 | 3.8 | 4.8 | 4.6 | 4.8 | 5 | 5 |
| 10 (Test Gel 1 + UT4) | 0 | 1.2 | 2.6 | 4 | 4.8 | 5 | 5 |
| 11 (Test Gel 2 + UT4) | 0 | 0 | 4.8 | 4.8 | 5 | 5 | 5 |

Transducers in ultrasound devices were later determined to be malfunctioning during the testing of Groups 4-7.
Group 9: 3 of 5 mice developed tissue damage lesions on the skin two days after three ultrasound treatments during the first week of the study. Ultrasound treatments were discontinued for this group, but daily topical minoxidil gel application continued. All tissue damage lesions healed after stopping ultrasound treatment.
Group 10: 2 of 5 mice developed skin lesion after two weeks (6 UT treatments. UT discontinued.
Group 11: No tissue damage lesions developed during study.

The average mouse hair coverage score per group as shown in Table 7 demonstrates that mice skin treated with Test Gel 2 and ultrasound treatment at a frequency of 700 kHz and angle of 15 degrees for 30 Seconds (Group 11) achieved a faster degree of terminal hair coverage at day 24 than any of the treatment regimens of Groups 1-10 without formation of tissue damage lesions. Notably, the treatment regimen of Group 11 achieved a faster degree of terminal hair coverage at day 24 than the mice treated with Test Gel 2 alone (i.e., without ultrasound treatment).

In contrast, focusing on the overall degree and speed of terminal hair coverage achieved over 45 day period, the treatment regimen of Group 10 (Test Gel 1 plus Ultrasound Treatment 3 [700 kHz, 90 Degree, 30 Seconds]) did not show the same hair growth coverage improvement versus Test Gel 1 alone (Group 2) as was shown with respect to the Test Gel 2 and ultrasound combination of Groups 9 and 11 (at 700 kHz; 90° and 15°, respectively; for 30 Seconds) versus treatment with Test Gel 2 alone (Group 3). This teaches that the formulation of Test Gel 2 contains ingredients which improve the combined treatment effect of Test Gel 2 combined with ultrasound (at 700 kHz; 90° and 15°, respectively; for 30 Seconds).

And, as noted by a comparison of the treatment regimens of Group 10 with Group 6 and a comparison of Group 11 with Group 7, Table 7 further shows that use of ultrasound at a frequency of 50 kHz and grazing angle of 15°, has less of an effect with when combined with either Test Gel 1 or Test Gel 2, on hair regrowth than use of ultrasound at a frequency of 700 kHz and grazing angle of 15° in combination with Test Gel 1 or Test Gel 2. Combining ultrasound at a frequency of 50 kHz (at grazing angle of 15°) with Test Gels 1 and 2 actually reduced the hair regrowth effects of using, Test Gel 1 or Test Gel 2 alone, respectively, as shown by comparing Group 6 with Group 2 and Group 7 with Group 3.

We claim:

1. A method for topically treating pain comprising the steps of:
    a. providing a topical composition comprising an analgesic active benefit agent;
    b. applying the topical composition to an area of the skin or scalp in need of treatment from the analgesic active benefit agent;
    c. providing a device having power source and an acoustic transducer electrically connected to the power source, the acoustic transducer calibrated to generate acoustic energy at a frequency ranging from about 20 kHz to about 3000 kHz;
    d. orienting the device such that any ultrasound waves generated by the acoustic transducer are projected at an angle e relative to the surface of the skin or scalp at the area on which the topical composition was applied, wherein the angle e is selected from the group consisting of 45°, 60° and 75°; and
    e. delivering the ultrasound to the area on which the topical composition was applied while maintaining the projection angle e relative to the surface of the skin or scalp at the area on which the topical composition was applied.

2. The method of claim 1, wherein the ultrasound is delivered for a period of time ranging from about 5 seconds to about 1 minute.

3. The method of claim 2, wherein the ultrasound is delivered for a period of time ranging from about 20 seconds to about 40 seconds.

4. The method of claim 1, wherein the frequency ranges from about 100 kHz to about 1000 kHz.

5. The method of claim 4, wherein the frequency ranges from about 250 kHz to about 750 kHz.

6. The method of claim 1, wherein the analgesic active benefit agent is ibuprofen.

* * * * *